US010206555B2

United States Patent
Kanda et al.

(10) Patent No.: US 10,206,555 B2
(45) Date of Patent: Feb. 19, 2019

(54) IMAGE PROCESSING APPARATUS, IMAGE PROCESSING METHOD, AND COMPUTER READABLE RECORDING MEDIUM

(71) Applicant: OLYMPUS CORPORATION, Tokyo (JP)

(72) Inventors: Yamato Kanda, Hino (JP); Takashi Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/989,233

(22) Filed: May 25, 2018

(65) Prior Publication Data

US 2018/0296064 A1    Oct. 18, 2018

Related U.S. Application Data

(63) Continuation of application No. PCT/JP2015/083294, filed on Nov. 26, 2015.

(51) Int. Cl.
*A61B 1/00* (2006.01)
*A61B 1/04* (2006.01)
(Continued)

(52) U.S. Cl.
CPC .......... *A61B 1/00009* (2013.01); *A61B 1/041* (2013.01); *G06K 9/4661* (2013.01); *G06T 7/0008* (2013.01); *G06T 7/13* (2017.01); *G06T 7/187* (2017.01); *G06T 7/40* (2013.01); *G06T 7/514* (2017.01); *G06T 7/60* (2013.01); *G16H 30/40* (2018.01); *G06T 2207/10068* (2013.01); *G06T 2207/20116* (2013.01)

(58) Field of Classification Search
CPC ........... G06T 7/187; G06T 7/514; G06T 7/13; G06T 7/0008; G06T 7/40; G06T 7/60; G16H 30/40; A61B 1/041; G06K 9/4661
See application file for complete search history.

(56) References Cited

U.S. PATENT DOCUMENTS 8,917,920 B2    12/2014  Matsuda et al.
2007/0225560 A1*    9/2007  Avni .................. A61B 1/00006
                                                              600/118

(Continued)

FOREIGN PATENT DOCUMENTS

JP    2005-192880 A    7/2005
JP    2007-125373 A    5/2007

(Continued)

OTHER PUBLICATIONS

International Search Report dated Feb. 23, 2016 issued in PCT/JP2015/083294.

(Continued)

*Primary Examiner* — Edward Park
(74) *Attorney, Agent, or Firm* — Scully, Scott, Murphy & Presser, P.C.

(57) ABSTRACT

An image processing apparatus includes: an abnormality candidate region detection unit that detects an abnormality candidate region based on a contour edge of a mucosal wall or a surface shape of the mucosal wall in an intraluminal image of a body; and an abnormal region specifying unit that specifies an abnormal region based on texture information of the abnormality candidate region.

15 Claims, 18 Drawing Sheets

(51) Int. Cl.
  *G06T 7/13* (2017.01)
  *G16H 30/40* (2018.01)
  *G06T 7/40* (2017.01)
  *G06T 7/187* (2017.01)
  *G06T 7/60* (2017.01)
  *G06T 7/00* (2017.01)
  *G06K 9/46* (2006.01)
  *G06T 7/514* (2017.01)

(56) References Cited

U.S. PATENT DOCUMENTS

| | | | |
|---|---|---|---|
| 2009/0003676 A1* | 1/2009 | Li | G06T 7/12 382/131 |
| 2009/0202124 A1 | 8/2009 | Matsuda et al. | |
| 2012/0008839 A1 | 1/2012 | Hirota et al. | |
| 2015/0092993 A1 | 4/2015 | Kanda et al. | |
| 2015/0254826 A1 | 9/2015 | Kanda et al. | |
| 2016/0217573 A1* | 7/2016 | Lian | G06T 5/20 |
| 2017/0046835 A1* | 2/2017 | Tajbakhsh | G06T 7/0012 |

FOREIGN PATENT DOCUMENTS

| | | |
|---|---|---|
| JP | 2008-093172 A | 4/2008 |
| JP | 2012-016453 A | 1/2012 |
| JP | 2013-255656 A | 12/2013 |
| JP | 2014-104293 A | 6/2014 |

OTHER PUBLICATIONS

International Search Report dated Feb. 23, 2016 received in PCT/JP2015/083294.

* cited by examiner

SI=0

SI=0.25

SI=0.5

SI=0.75

SI=1.0

IMAGE PROCESSING APPARATUS, IMAGE PROCESSING METHOD, AND COMPUTER READABLE RECORDING MEDIUM

CROSS-REFERENCE TO RELATED APPLICATION

This application is a continuation of International Application No. PCT/JP2015/083294, filed on Nov. 26, 2015, the entire contents of which are incorporated herein by reference.

BACKGROUND

The present disclosure relates to an image processing apparatus, and an image processing method, and a computer readable recording medium, which are configured to specify an abnormal region included in an image acquired by capturing the interior of a body lumen.

A technique for detecting an abnormal portion (for example, a polyp, or the like) in an image obtained by capturing the interior of a body lumen using a medical observation device such as an endoscope and a capsule endoscope (hereinafter referred to as an "intraluminal image") is known (for example, JP 2007-125373 A). In this technique, edge extraction is performed on the intraluminal image, then an elliptical geometric shape is identified using Hough transform or the like, and an abnormal portion is detected based on a color of the shape.

SUMMARY

An image processing apparatus according to one aspect of the present disclosure includes: an abnormality candidate region detection unit that detects an abnormality candidate region based on a contour edge of a mucosal wall or a surface shape of the mucosal wall in an intraluminal image of a body; and an abnormal region specifying unit that specifies an abnormal region based on texture information of the abnormality candidate region, wherein the abnormal region specifying unit includes: an information calculation region setting unit that sets a calculation region for calculation of the texture information; a texture information calculation unit that calculates the texture information in the calculation region; and an identification unit that identifies the abnormal region based on the texture information, the texture information calculation unit includes: an imaging distance normalization unit that performs normalization in accordance with an imaging distance to the calculation region; and a light absorption change structure feature data calculation unit that calculates feature data based on a light absorption change structure in the calculation region, and the light absorption change structure feature data calculation unit includes: a light absorption change information calculation unit that calculates light absorption change information in the calculation region; a ductal structure region specifying unit that specifies a ductal structure region based on the light absorption change information; and a fleck structure region specifying unit that specifies a fleck structure region based on the light absorption change information.

An image processing method according to another aspect of the present disclosure includes: an abnormality candidate region detection step of detecting an abnormality candidate region based on a contour edge of a mucosal wall or a surface shape of the mucosal wall in an intraluminal image of a body; and an abnormal region specifying step of specifying an abnormal region based on texture information of the abnormality candidate region, wherein the abnormal region specifying step includes: an information calculation region setting step of setting a calculation region for calculation of the texture information; a texture information calculation step of calculating the texture information in the calculation region; and an identification step of identifying the abnormal region based on the texture information, the texture information calculation step includes: an imaging distance normalization step of performing normalization in accordance with an imaging distance to the calculation region; and a light absorption change structure feature data calculation step of calculating feature data based on a light absorption change structure in the calculation region, and the light absorption change structure feature data calculation step includes: an light absorption change information calculation step of calculating light absorption change information in the calculation region; a ductal structure region specifying step of specifying a ductal structure region based on the light absorption change information; and a fleck structure region specifying step of specifying a fleck structure region based on the light absorption change information.

A non-transitory computer-readable recording medium records an executable program according to another aspect of the present invention, the program instructing a processor of an image processing apparatus to execute: detecting an abnormality candidate region based on a contour edge of a mucosal wall or a surface shape of the mucosal wall in an intraluminal image of a body; specifying an abnormal region based on texture information of the abnormality candidate region; setting a calculation region for calculation of the texture information; calculating the texture information in the calculation region; identifying the abnormal region based on the texture information; performing normalization in accordance with an imaging distance to the calculation region; calculating feature data based on a light absorption change structure in the calculation region; calculating light absorption change information in the calculation region; specifying a ductal structure region based on the light absorption change information; and specifying a fleck structure region based on the light absorption change information.

The above and other features, advantages and technical and industrial significance of this disclosure will be better understood by reading the following detailed description of presently preferred embodiments of the disclosure, when considered in connection with the accompanying drawings.

DETAILED DESCRIPTION

First Embodiment

Configuration of Image Processing Apparatus

Figure 1:
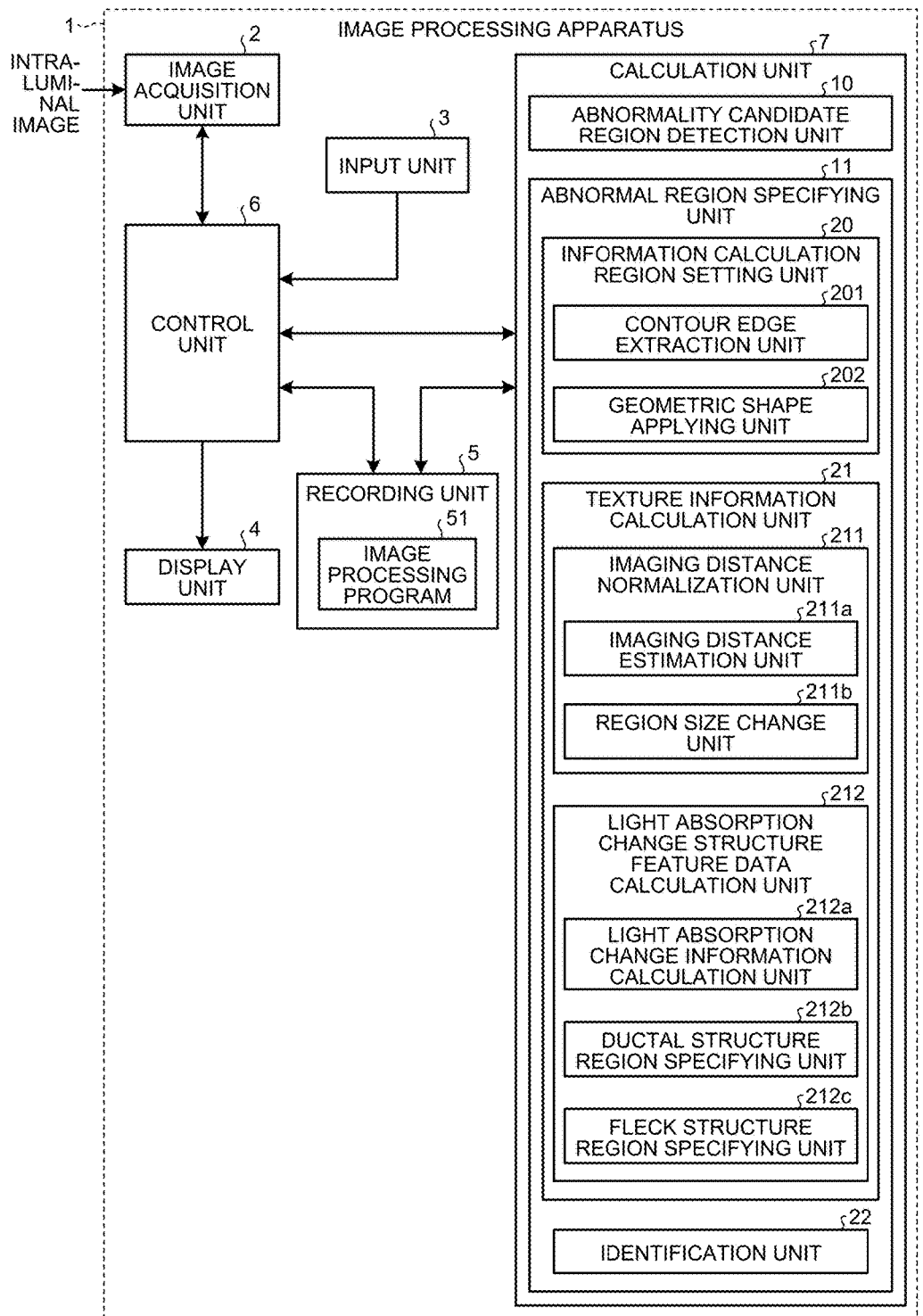
FIG. 1 is a block diagram illustrating a configuration of an image processing apparatus according to a first embodiment.

FIG. 1 is a block diagram illustrating a configuration of an image processing apparatus according to a first embodiment. For example, an image processing apparatus 1 illustrated in FIG. 1 is an apparatus that performs image processing to detect an abnormal region (abnormal part) recognizable from a mucosal surface or an abnormal region (abnormal part) present on a mucosa (hereinafter simply referred to as the "abnormal region recognizable from the mucosal surface") from an intraluminal image acquired by capturing a body lumen using an endoscope (endoscopic scope) or a capsule endoscope (hereinafter collectively referred to as simply as the "endoscope"). In addition, hereinafter, the intraluminal image is usually a color image having predetermined (for example, 256 tones) pixel levels (pixel values) for each wavelength component (color component) of R (red), G (green), and B (blue) at each pixel position.

The image processing apparatus 1 illustrated in FIG. 1 includes: an image acquisition unit 2 that acquires image data corresponding to the intraluminal image captured by the endoscope from the endoscope or the outside; an input unit 3 that receives an input signal input by an external operation; a display unit 4 that displays the intraluminal image and performs various types of display; a recording unit 5 that records the image data and various programs acquired by the image acquisition unit 2; a control unit 6 that controls the overall operation of the image processing apparatus 1; and an calculation unit 7 that performs predetermined image processing on the image data.

The image acquisition unit 2 is appropriately configured in accordance with a mode of a system including the endoscope. For example, in a case where a portable recording medium is used for exchange of image data with the endoscope, the image acquisition unit 2 is configured as a reader device which is equipped with the recording medium detachably and reads the recorded image data. In addition, in the case of using a server that records the image data captured by the endoscope, the image acquisition unit 2 is configured as a communication device capable of bidirectionally communicating with this server, or the like and acquires the image data by performing data communication with the server. Furthermore, the image acquisition unit 2 may be configured as an interface device or the like to which the image data is input from the endoscope via a cable or the like.

The input unit 3 is realized by input devices, for example, a keyboard, a mouse, a touch panel, various switches and the like, and outputs an input signal, received in response to an external operation, to the control unit 6.

The display unit 4 is realized by a display device such as a display panel of liquid crystal or organic electro luminescence (EL), and displays various screens including the intraluminal image under the control of the control unit 6.

The recording unit 5 is realized by various IC memories such as a flash memory, a read only memory (ROM), and a random access memory (RAM), a hard disk that is built-in or connected by a data communication terminal, and the like. The recording unit 5 stores a program configured to operate the image processing apparatus 1 and to cause the image processing apparatus 1 to execute various functions, data to be used during the execution of the program, and the like in addition to image data acquired by the image acquisition unit 2. For example, the recording unit 5 records an image processing program 51 to detect the abnormal region recognizable from the mucosal surface such as a polyp, and various types of information used during execution of the program.

The control unit 6 is realized using a central processing unit (CPU) or the like, and comprehensively performs the overall operation of the image processing apparatus 1 to transfer an instruction and data transfer to the respective units constituting the image processing apparatus 1 in accordance with the image data input from the image acquisition unit 2, the input signal input from the input unit 3, and the like by reading various programs recorded in the recording unit 5.

The calculation unit 7 is realized using a CPU or the like, performs image processing on the intraluminal image by reading the image processing program recorded by the recording unit 5, executes the image processing to detect the abnormal region recognizable from the mucosal surface such as a polyp, and outputs a result of such image processing to the control unit 6.

Detailed Configuration of Calculation Unit

Next, a detailed configuration of the calculation unit 7 will be described.

The calculation unit 7 includes an abnormality candidate region detection unit 10 and an abnormal region specifying unit 11.

The abnormality candidate region detection unit 10 detects an abnormality candidate region based on a contour edge of a mucosal wall in the intraluminal image of a living body.

The abnormal region specifying unit 11 specifies an abnormal region based on texture information (pattern) of the abnormality candidate region. The abnormal region specifying unit 11 includes an information calculation region setting unit 20, a texture information calculation unit 21, and an identification unit 22.

The information calculation region setting unit 20 sets a texture information calculation region for calculating texture information with respect to the abnormality candidate region. The information calculation region setting unit 20 includes a contour edge extraction unit 201 and a geometric shape applying unit 202.

The contour edge extraction unit 201 extracts a contour edge of the mucosal wall.

The geometric shape applying unit 202 applies a geometric shape to be applied in the contour edge extracted by the contour edge extraction unit 201. For example, the geometric shape applying unit 202 applies a shape such as an ellipse and a circle to be applied in the contour edge extracted by the contour edge extraction unit 201.

The texture information calculation unit 21 calculates the texture information in the texture information calculation region. The texture information calculation unit 21 includes an imaging distance normalization unit 211 and a light absorption change structure feature data calculation unit 212.

The imaging distance normalization unit 211 performs normalization in accordance with the imaging distance to the texture information calculation region. The imaging distance normalization unit 211 has an imaging distance estimation unit 211a and a region size change unit 211b.

The imaging distance estimation unit 211a estimates the imaging distance from an imaging unit of the endoscope or the like to the texture information calculation region.

The region size change unit 211b changes a region size of the texture information calculation region based on the imaging distance estimated by the imaging distance estimation unit 211a.

The light absorption change structure feature data calculation unit 212 calculates feature data based on a light absorption change structure in the texture information calculation region. The light absorption change structure feature data calculation unit 212 includes a light absorption change information calculation unit 212a, a ductal structure region specifying unit 212b, and a fleck structure region specifying unit 212c.

The light absorption change information calculation unit 212a calculates light absorption change information in the texture information calculation region.

The ductal structure region specifying unit 212b specifies a ductal structure region based on the absorption change information calculated by the light absorption change information calculation unit 212a.

The fleck structure region specifying unit 212c specifies a fleck structure region based on the light absorption change information calculated by the light absorption change information calculation unit 212a.

When a proportion of the fleck structure region in the entire texture information calculation region is larger than a predetermined value, the identification unit 22 determines that the abnormality candidate region detected by the abnormality candidate region detection unit 10 is abnormal.

Processing of Image Processing Apparatus

Figure 2:
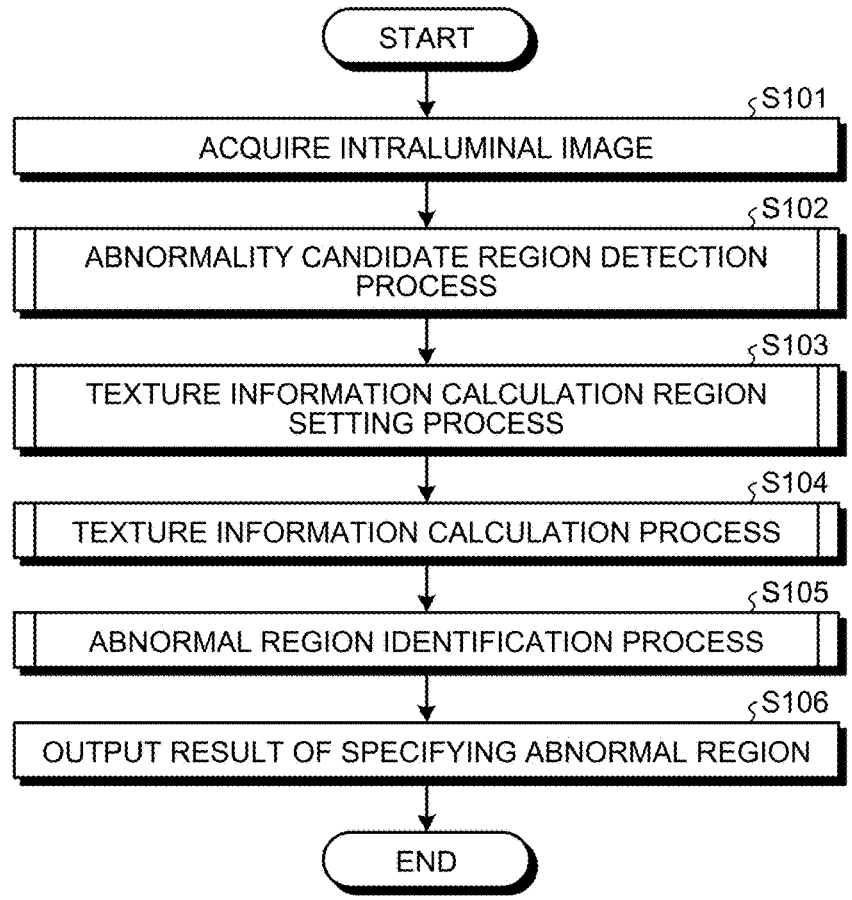
FIG. 2 is a flowchart illustrating an outline of processing executed by the image processing apparatus according to the first embodiment.

A description will be given regarding an image processing method for detecting an abnormal region on an intraluminal image executed by the image processing apparatus 1 configured in this manner. FIG. 2 is a flowchart illustrating an outline of processing executed by the image processing apparatus 1.

As illustrated in FIG. 2, the image processing apparatus 1 first acquires the intraluminal image corresponding to the image data captured by the endoscope or the like from the outside via the image acquisition unit 2, and records the acquired intraluminal image in the recording unit 5 (Step S101).

Subsequently, the abnormality candidate region detection unit 10 acquires the image data of the intraluminal image recorded in the recording unit 5, and executes an abnormality candidate region detection process to detect a candidate for an abnormal region from the acquired intraluminal image (Step S102).

Figure 3:
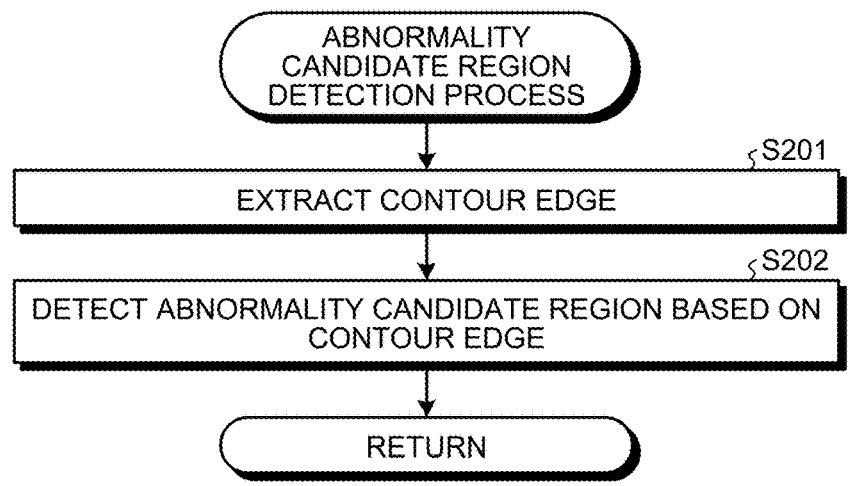
FIG. 3 is a flowchart illustrating an outline of an abnormality candidate region detection process of FIG. 2.

FIG. 3 is a flowchart illustrating an outline of the abnormality candidate region detection process in Step S102 of FIG. 2.

Figure 4:
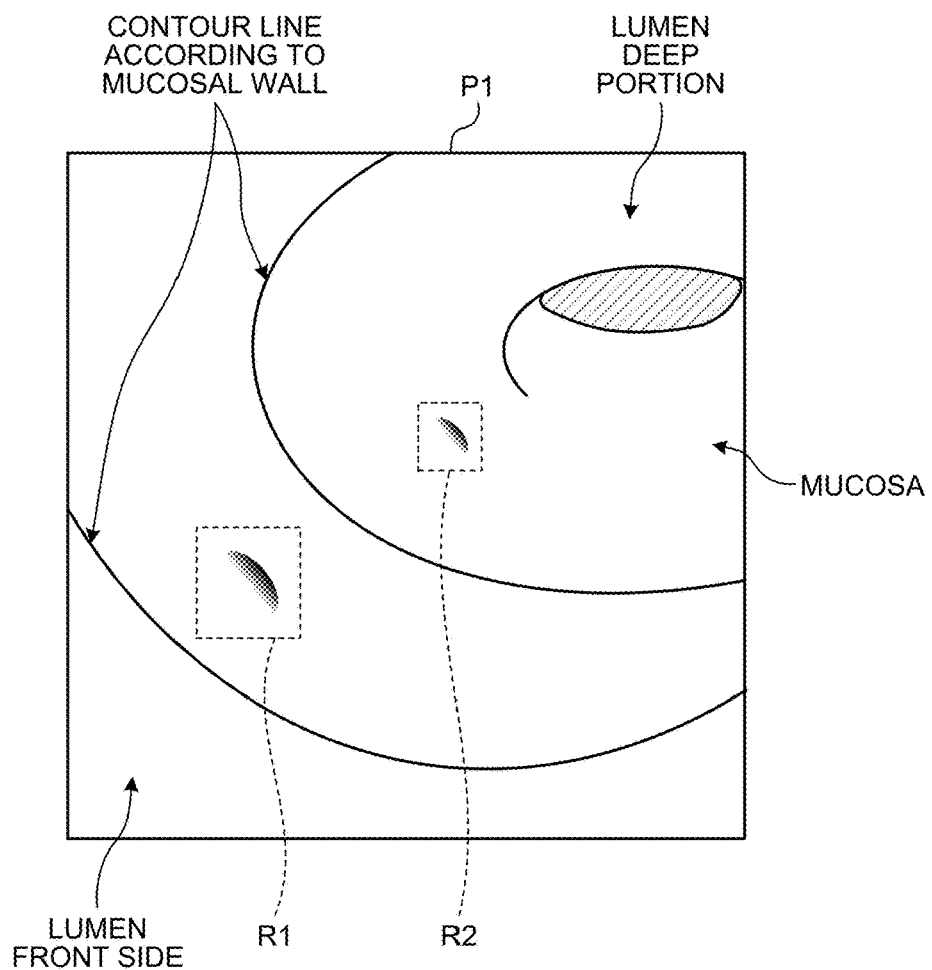
FIG. 4 is a view illustrating an example of an intraluminal image.

As illustrated in FIG. 3, the abnormality candidate region detection unit 10 extracts a contour edge of a mucosal wall in the intraluminal image (Step S201), and detects an abnormality candidate region based on the extracted contour edge of the mucosal wall (Step S202). More specifically, first, a low absorption wavelength component (for example, an R component) having the lowest degree of absorption and scattering in a body is selected, known edge extraction processing (see: CG-ARTS Association: Digital Image processing: 114P, Edge Extraction: 209P, Contour Line Detection) is applied to this low absorption wavelength component to extract the contour edge of the mucosal wall. Then, a region forming an arc shape at the contour edge is detected, and a contour edge serving as an abnormality candidate is specified based on the area of the region forming the arc shape, curvature information thereof, or the like (for example, see JP 2007-244519 A). Then, a peripheral region including this edge is detected as the abnormality candidate region. Incidentally, extraction of abnormal findings based on contour information disclosed in JP 2005-192880 A may be applied. As a result, the abnormality candidate region detection unit 10 detects an abnormality candidate region R1 and an abnormality candidate region R2 based on contour edges of mucosal walls in an intraluminal image P1 as illustrated in FIG. 4. Incidentally, the endoscope often performs imaging obliquely to the mucosal surface of the inner wall of the body as illustrated in the intraluminal image P1 in FIG. 4. Thus, a portion from a mucosal surface on a ductal front side where the imaging distance is close to a mucosal surface in a ductal deep portion where the imaging distance is distant is reflected in the intraluminal image P1 captured by the endoscope, and a close object is reflected to be larger than a distant object as illustrated in FIG. 4. After Step S202, the image processing apparatus 1 returns to the main routine of FIG. 2.

Returning to FIG. 2, the description regarding Step S103 and the subsequent steps will be continued.

In Step S103, the information calculation region setting unit 20 executes a texture information calculation region setting process to calculate texture information (pattern) of the abnormality candidate region detected by the abnormality candidate region detection unit 10.

Figure 5:
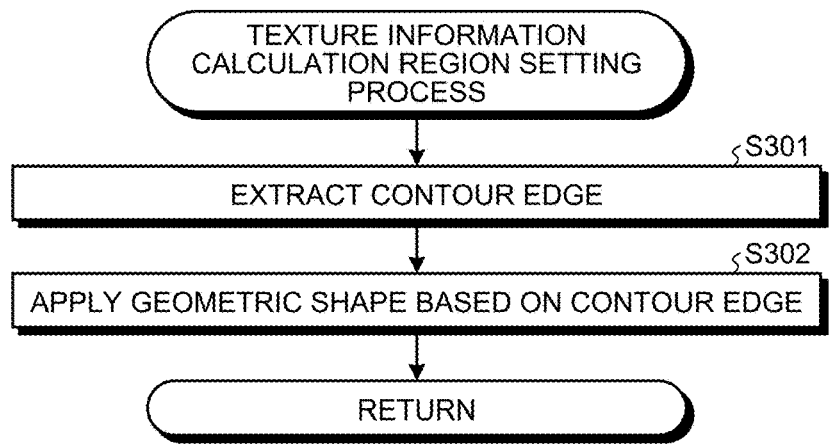
FIG. 5 is a flowchart illustrating an outline of a texture information calculation region setting process of FIG. 2.

FIG. 5 is a flowchart illustrating an outline of the texture information calculation region setting process in Step S103 of FIG. 2.

As illustrated in FIG. 5, the contour edge extraction unit 201 extracts a contour edge of a mucosal wall of a lumen in the abnormality candidate region detected by the abnormality candidate region detection unit 10 (Step S301). More specifically, the low absorption wavelength component (for example, the R component) having the lowest degree of absorption and scattering in the body is selected, and the above-described edge extraction is performed on the selected low absorption wavelength component to extract the contour edge of the mucosal wall. Alternatively, three-dimensional pixel value information disclosed in JP 2012-11137 A is obtained, and the edge extraction process is applied thereto. Alternatively, a contour edge extraction method disclosed in JP 2014-104293 may be used.

Figure 6A:
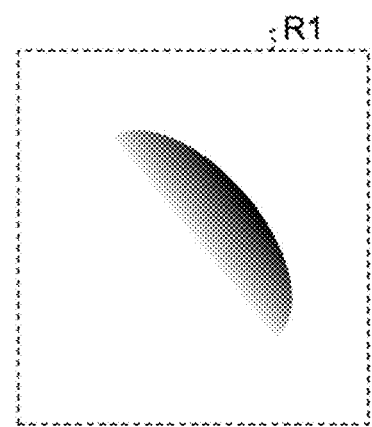
FIG. 6A is a view illustrating an example of an abnormality candidate region.
Figure 6B:
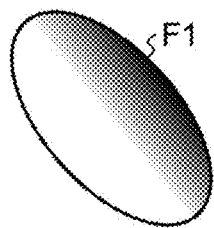
FIG. 6B is a view schematically illustrating applying of a geometric shape with respect to the abnormality candidate region.

Subsequently, the geometric shape applying unit 202 applies the geometric shape based on the contour edge extracted by the contour edge extraction unit 201 (Step S302). More specifically, a geometric shape F1 (for example, an ellipse) is applied to the contour edge extracted from the abnormality candidate region R1 by the contour edge extraction unit 201 (FIG. 6A→FIG. 6B). A region in the applied ellipse is a region that is more likely to contain advantageous texture information for specifying the abnormal region than other peripheral regions in the abnormality candidate region R1. As a result, the information calculation region setting unit 20 can set a texture information calculation region to calculate the advantageous texture information by specifying the abnormal region. After Step S302, the image processing apparatus 1 returns to the main routine of FIG. 2.

Returning to FIG. 2, the description regarding Step S104 and the subsequent steps will be continued.

In Step S104, the texture information calculation unit 21 executes a texture information calculation process to calculate texture information of the texture information calculation region.

Figure 7:
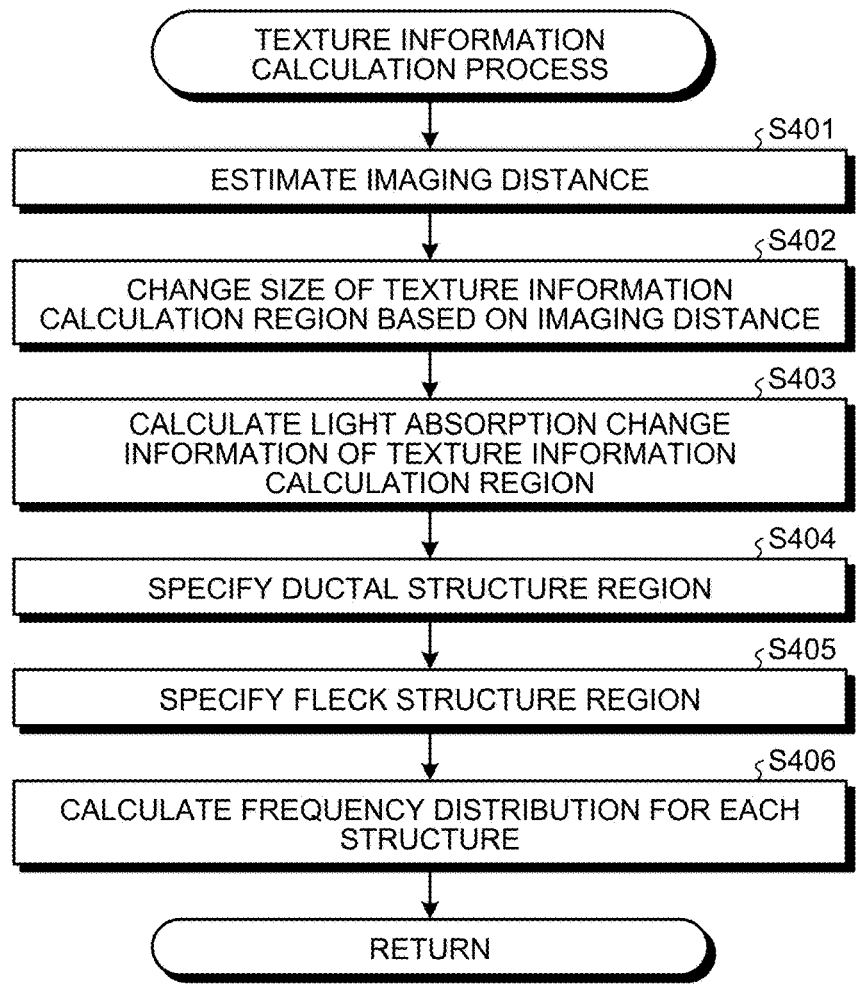
FIG. 7 is a flowchart illustrating an outline of a texture information calculation process of FIG. 2.

FIG. 7 is a flowchart illustrating an outline of the texture information calculation process in Step S104 of FIG. 2.

As illustrated in FIG. 7, the imaging distance estimation unit 211a estimates an imaging distance to the texture information calculation region (Step S401). More specifically, the imaging distance assuming a uniform diffusion surface is estimated according to the following Formula (1) based on a pixel value of the low absorption wavelength component (such as the R component) of a pixel in the texture information calculation region. Although the imaging distance can be calculated for each pixel, an average value or the like thereof is used as a representative imaging distance with respect to the texture information calculation region.

$$r = \sqrt{\frac{I \times K \times \cos\theta}{L}} \quad (1)$$

Here, r represents an imaging distance, I represents a radiation intensity (measured in advance) of a light source, K represents a diffusion reflection coefficient (an average value thereof is measured in advance) of the mucosal surface, θ represents an angle formed between a normal vector of the mucosal surface and a vector from the surface to the light source (which is a value determined by a positional relationship between the light source at a distal end of the endoscope and the mucosal surface, and an average value thereof is set in advance), and L represents a pixel value of a low absorption wavelength component (R component) of a pixel in which an imaging distance estimation target appears.

Figure 8:
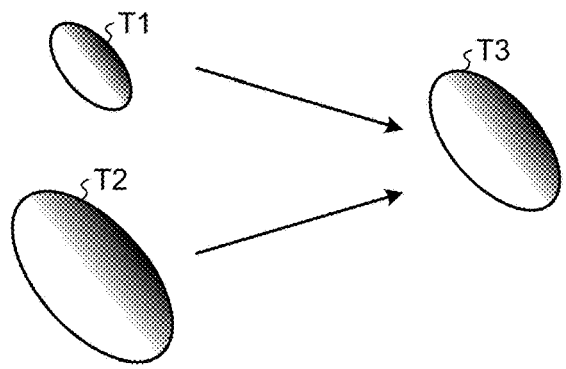
FIG. 8 is a view schematically illustrating an outline of a size change using a region size change unit.

Subsequently, the region size change unit 211b changes a size of the texture information calculation region based on the imaging distance estimated by the imaging distance estimation unit 211a (Step S402). More specifically, the size is changed so as to be a size at the time of performing capturing from the same imaging distance with respect to the texture information calculation region whose size on an image changes depending on closeness of the imaging distance. For example, as illustrated in FIG. 8, both a texture information calculation region T1 which appears small since the imaging distance is distant and a texture information calculation region T2 which appears large since the imaging distance is close have the same size, for example, to form a texture information calculation region T3. As a result, the imaging distance normalization unit 211 can normalize the texture information calculation region set by the information calculation region setting unit 20 in accordance with the imaging distance.

Thereafter, the light absorption change information calculation unit 212a calculates light absorption change information of the texture information calculation region whose size has been changed by the region size change unit 211b (Step S403). More specifically, for each pixel in the texture information calculation region whose size has been changed, a G component or a B component close to an absorption band (wavelength) of hemoglobin in the body is selected and set as the light absorption change information. Incidentally, a value having a high correlation with the light absorption change information, such as a value calculated secondarily by already-known conversion, a luminance, a color difference (YCbCr conversion), a hue, saturation, lightness (HSI conversion), and a color ratio, may be used based on RGB components of each pixel in the texture information calculation region.

Figure 9:
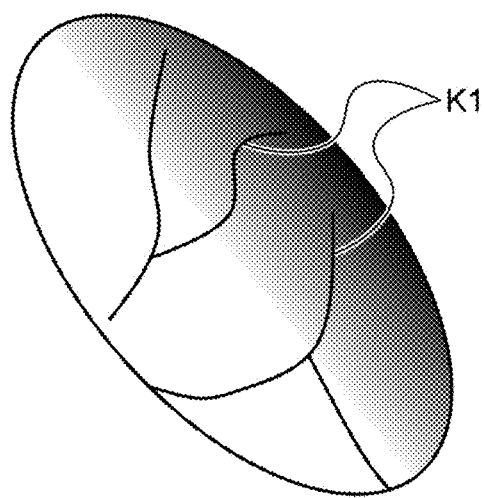
FIG. 9 is a view schematically illustrating specifying of a ductal structure region by a ductal structure region specifying unit.
Figure 10A:
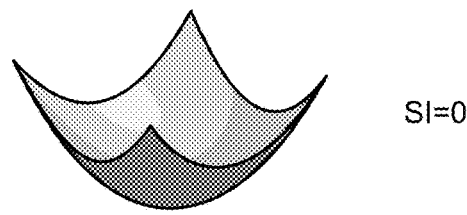
FIG. 10A is a view schematically illustrating a shape of a shape index.
Figure 10B:
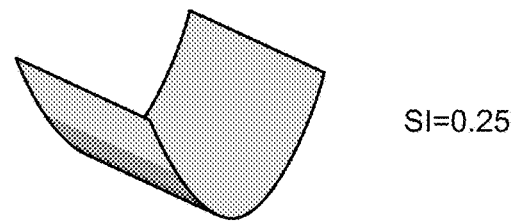
FIG. 10B is a view schematically illustrating a shape of a shape index.
Figure 10C:
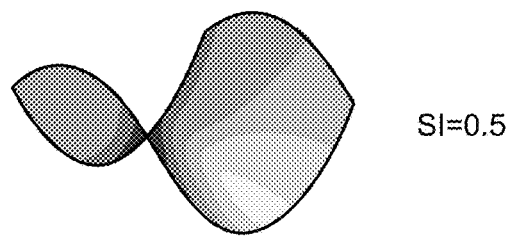
FIG. 10C is a view schematically illustrating a shape of a shape index.
Figure 10D:
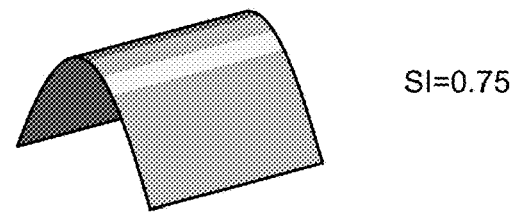
FIG. 10D is a view schematically illustrating a shape of a shape index.
Figure 10E:
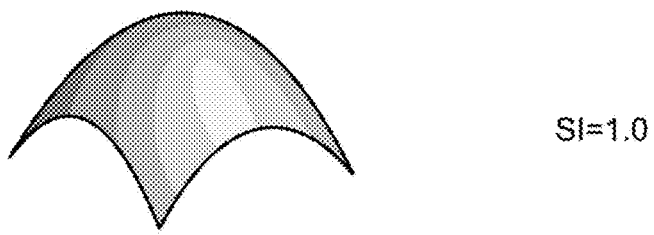
FIG. 10E is a view schematically illustrating a shape of a shape index.
Figure 11A:
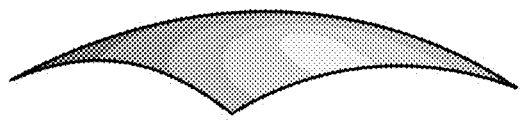
FIG. 11A is a view schematically illustrating a shape corresponding to a curvedness value.
Figure 11B:
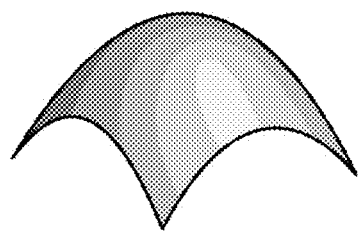
FIG. 11B is a view schematically illustrating a shape corresponding to a curvedness value.
Figure 11C:
FIG. 11C is a view schematically illustrating a shape corresponding to a curvedness value.

Subsequently, the ductal structure region specifying unit 212b specifies the ductal structure region based on the absorption change information calculated by the light absorption change information calculation unit 212a (Step S404). More specifically, a ductal structure region K1 in which a ductal structure of a blood vessel or the like appears is specified in the texture information calculation region as illustrated in FIG. 9. In practice, a shape index or curvedness (see MEDICAL IMAGING TECHNOLOGY Vol. 19 No. 3 May 2001), which is a known three-dimensional curvature feature, is calculated based on, for example, the eigenvalues of the Hessian matrix disclosed in International Application PCT/JP2015/067080 (incidentally, see the international application PCT/JP2015/067080 concerning a process of calculating the eigenvalue). The value of the shape index (SI) corresponds to a regional shape (a cup, a rut, a saddle, a ridge, or a cap) of the light absorption change information as illustrated in FIGS. 10A to 10E. In addition, a value of the curvedness corresponds to a regional shape (flat to sharp) of the light absorption change information as illustrated in FIGS. 11A to 11C. Thus, a ductal structure region in which a ductal structure of a blood vessel or the like appears is specified based on these values. Incidentally, the ductal structure region specifying unit 212b may specify a ductal structure region by using a correlation with a model of a pixel value change shape corresponding to the ductal structure, calculating well-known uniform local binary pattern (ULBP) feature data, Gabor feature data, or the like, or calculating a change profile of the light absorption change information in a plurality of directions with respect to a pixel of interest.

Figure 12:
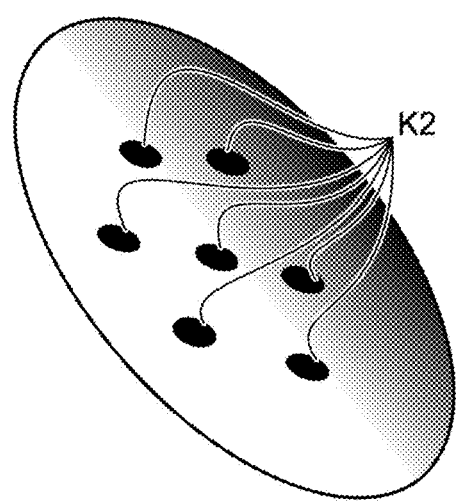
FIG. 12 is a view schematically illustrating specifying of a fleck structure region by a fleck structure region specifying unit.

Thereafter, the fleck structure region specifying unit 212c specifies a fleck structure region based on the light absorption change information calculated by the light absorption change information calculation unit 212a (Step S405). More specifically, a fleck structure region K2 in which a capillary vessel in a glandular structure appears is specified in the texture information calculation region as illustrated in FIG. 12. In practice, the fleck structure is specified based on the method illustrated in the specifying of the ductal structure region. Incidentally, when the correlation with the model of the pixel value change shape is used, the model corresponding to the fleck structure is used.

Subsequently, the light absorption change structure feature data calculation unit 212 calculates a frequency distribution for each structure of the ductal structure region and the fleck structure region (Step S406). More specifically, frequency distributions (area distributions) of the ductal structure region, the fleck structure region, and other unstructured regions in the texture information calculation region are calculated as illustrated in FIG. 12. In this manner, the light absorption change structure feature data calculation unit 212 calculates the frequency distribution for each structure as light absorption change structure feature data of the texture information calculation region. After Step S406, the image processing apparatus 1 returns to the main routine in FIG. 2.

Returning to FIG. 2, the description of Step S105 and the subsequent steps will be continued.

In Step S105, the identification unit 22 executes abnormal region identification process for identifying an abnormal region based on the light absorption change structure feature data.

Figure 14:
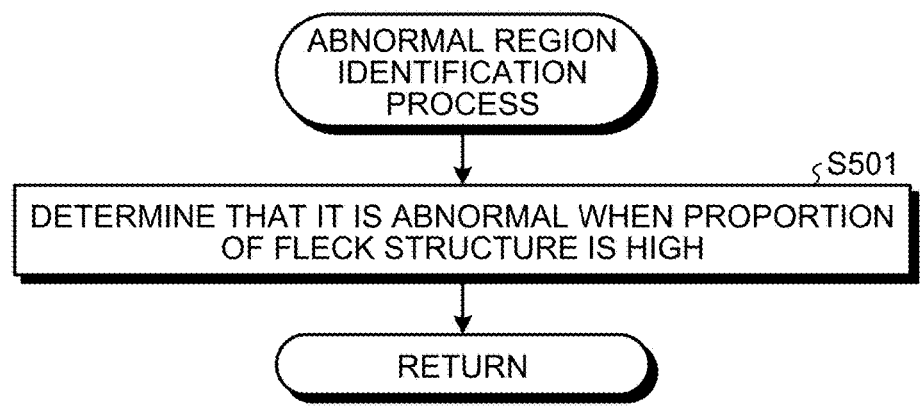
FIG. 14 is a flowchart schematically illustrating an outline of an abnormal region identification process in FIG. 2.

FIG. 14 is a flowchart illustrating an outline of the abnormal region identification process in Step S105 of FIG. 2.

Figure 13:
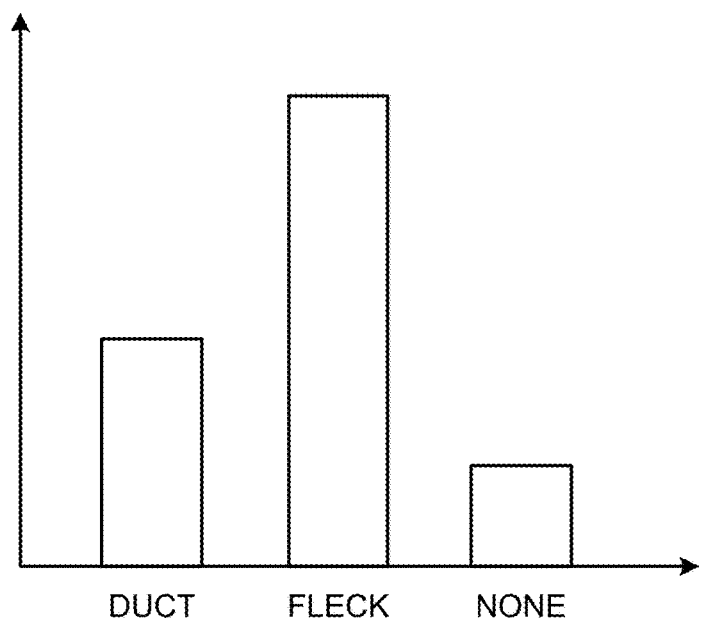
FIG. 13 is a view illustrating an example of a frequency distribution for each structure.

As illustrated in FIG. 14, the identification unit 22 determines whether a proportion of the fleck structure in the entire texture information calculation region is larger than a predetermined value based on the light absorption change structure feature data, and determines that the abnormality candidate region detected by the abnormality candidate region detection unit 10 is abnormal (Step S501) when the proportion of the fleck structure is larger than the predetermined value (see, for example, FIG. 13). After Step S501, the image processing apparatus 1 returns to the main routine in FIG. 2.

Returning to FIG. 2, the description of Step S106 and the subsequent steps will be continued.

In Step S106, the calculation unit 7 outputs an identification result of the abnormal region to the display unit 4. After Step S106, the image processing apparatus 1 ends the present processing.

According to the first embodiment described above, the abnormality candidate region detection unit 10 detects the abnormality candidate region based on the contour edge of the mucosal wall, and the abnormal region specifying unit 11 specifies the abnormal region based on the texture information of the abnormality candidate region, it is possible to sufficiently secure the performance of detecting the abnormal part.

First Modification

Next, a first modification according to the first embodiment will be described. The first modification according to the first embodiment has a different configuration and a different process to be executed from those the information calculation region setting unit 20. Hereinafter, the process executed by an information calculation region setting unit according to the first modification of the first embodiment will be described after describing the configuration of the information calculation region setting unit according to the first modification of the first embodiment. Incidentally, the same configurations as those of the image processing apparatus 1 according to the first embodiment will be denoted by the same reference signs, and the description thereof will be omitted.

Figure 15:
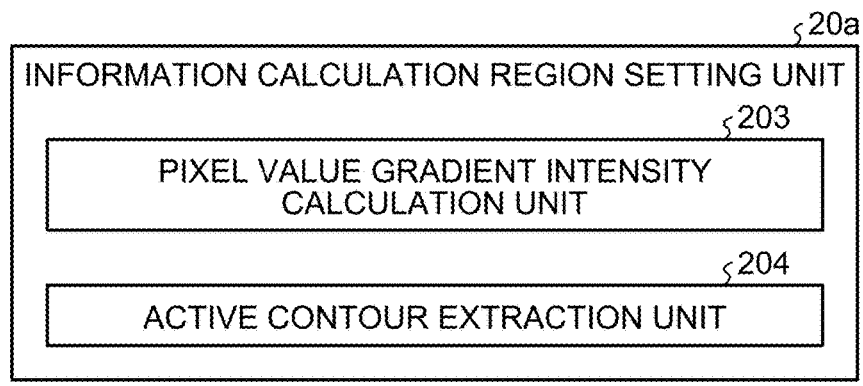
FIG. 15 is a block diagram illustrating a configuration of an information calculation region setting unit according to a first modification of the first embodiment.

FIG. 15 is a block diagram illustrating the configuration of the information calculation region setting unit according to the first modification of the first embodiment. An information calculation region setting unit 20a illustrated in FIG. 15 includes a pixel value gradient intensity calculation unit 203 and an active contour extraction unit 204.

The pixel value gradient intensity calculation unit 203 calculates pixel value gradient intensity of a pixel in an abnormality candidate region.

The active contour extraction unit 204 performs active contour extraction based on the pixel value gradient intensity.

Figure 16:
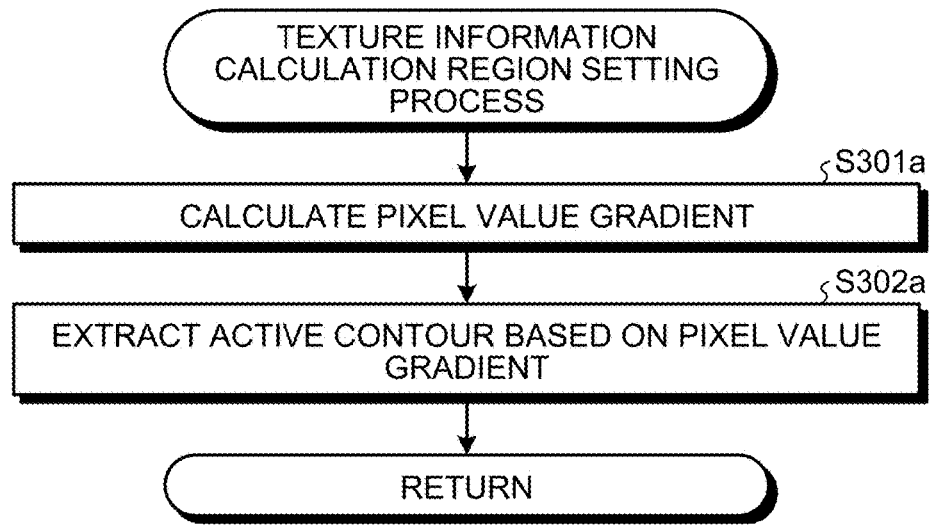
FIG. 16 is a flowchart illustrating an outline of a texture information calculation region setting process executed by an information calculation region setting unit according to the first modification of the first embodiment.

Next, a texture information calculation region setting process executed by the information calculation region setting unit 20a will be described. FIG. 16 is a flowchart illustrating an outline of the texture information calculation region setting process executed by the information calculation region setting unit 20a. Incidentally, processes of the first modification of the first embodiment are the same as the processes (see FIG. 2) executed by the image processing apparatus 1 according to the first embodiment described above except for the texture information calculation region setting process executed by the information calculation region setting unit 20a, and thus, the description thereof will be omitted.

As illustrated in FIG. 16, the pixel value gradient intensity calculation unit 203 calculates pixel value gradient intensity of a pixel in the abnormality candidate region (Step S301a).

Subsequently, the active contour extraction unit 204 performs active contour extraction (see: CG-ARTS Association: Digital Image processing: P196 to P199, Region Division Processing Using Edge Between Object and Background) based on the pixel value gradient intensity of the abnormality candidate region (Step S302a). As a result, a closed region is set such that the contour to be applied in a portion having the high pixel value gradient intensity within the abnormality candidate region (see, for example, FIGS. 6A and 6B). After Step S302a, the image processing apparatus 1 returns to the main routine in FIG. 2.

According to the first modification of the first embodiment described above, it is possible to extract a region that is highly likely to contain advantageous texture information for specifying an abnormal region in the abnormality candidate region by the active contour extraction and to sufficiently secure the performance of detecting an abnormal part.

Second Modification

A second modification of the first embodiment will be described. The second modification according to the first embodiment has a different configuration of an information calculation region setting unit, and a different process executed by the information calculation region setting unit. Hereinafter, the process executed by an information calculation region setting unit according to the second modification of the first embodiment will be described after describing the configuration of the information calculation region setting unit according to the second modification of the first embodiment.

Figure 17:
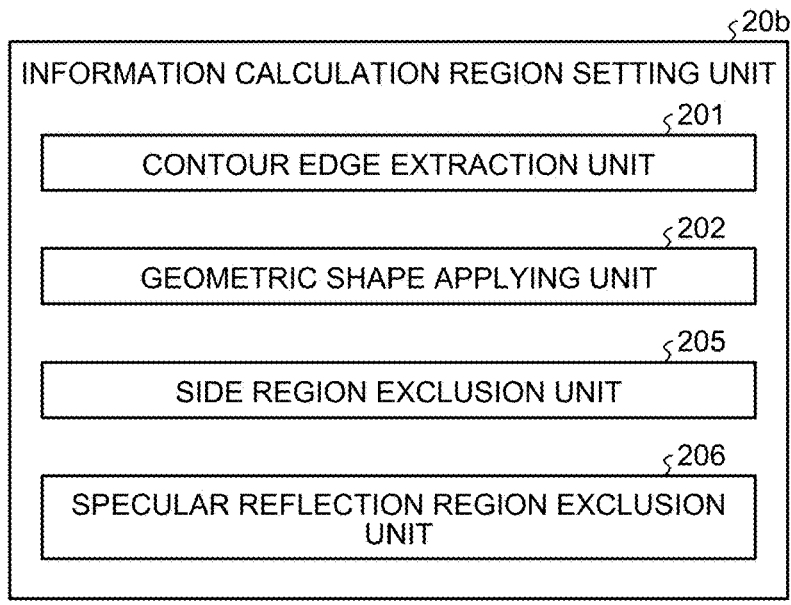
FIG. 17 is a block diagram illustrating a configuration of an information calculation region setting unit according to a second modification of the first embodiment.

FIG. 17 is a block diagram illustrating a configuration of the information calculation region setting unit according to the second modification of the first embodiment. An information calculation region setting unit 20b illustrated in FIG. 17 further includes a side region exclusion unit 205 and a specular reflection region exclusion unit 206, in addition to the configuration of the information calculation region setting unit 20 according to the first embodiment described above.

The side region exclusion unit 205 excludes a side region obtained by obliquely capturing a mucosal wall in an abnormality candidate region.

The specular reflection region exclusion unit 206 excludes a specular reflection region in the abnormality candidate region.

Figure 18:
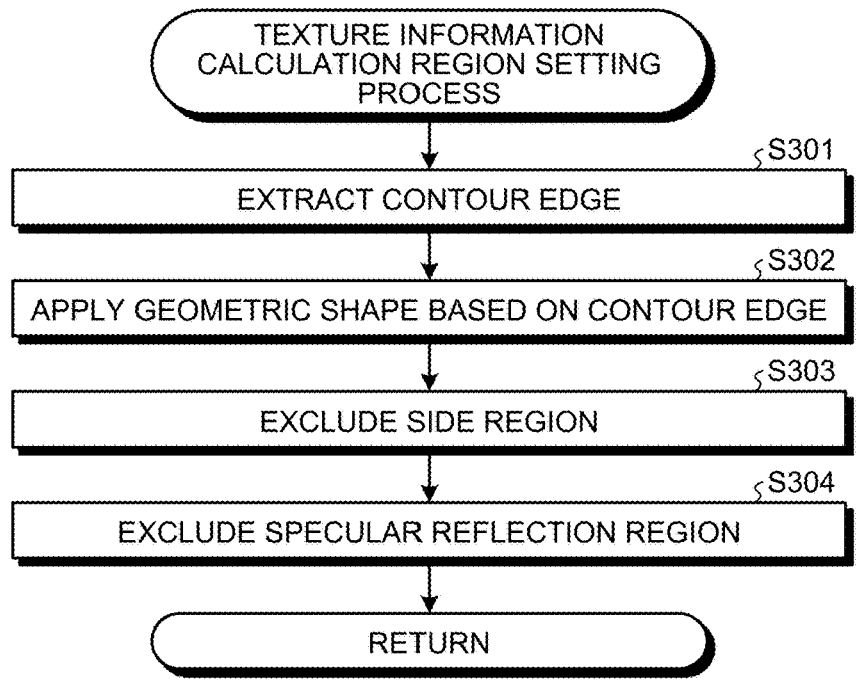
FIG. 18 is a flowchart illustrating an outline of a texture information calculation region setting process executed by an information calculation region setting unit according to the second modification of the first embodiment.

Next, a texture information calculation region setting process executed by the information calculation region setting unit 20b will be described. FIG. 18 is a flowchart illustrating an outline of the texture information calculation region setting process executed by the information calculation region setting unit 20b. Incidentally, the texture information calculation region setting process executed by the information calculation region setting unit 20b according to the second modification of the first embodiment further executes Steps S303 and S304 in addition to Steps S301 and S302 of the texture information calculation region setting process (see FIG. 5) according to the first embodiment described above. Thus, Steps S303 and S304 will be described hereinafter. In addition, processes of the second modification of the first embodiment are the same as the processes (see FIG. 2) executed by the image processing apparatus 1 according to the first embodiment described above except for the texture information calculation region setting process executed by the information calculation region setting unit 20b, and thus, the description thereof will be omitted.

Figure 19A:
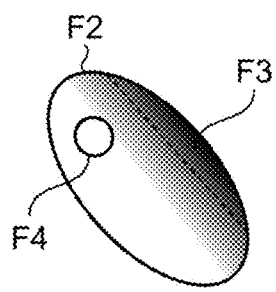
FIG. 19A is a view schematically illustrating exclusion of a side region of an abnormality candidate region by a side region exclusion unit according to the second modification of the first embodiment.

In Step S303, the side region exclusion unit 205 excludes a side region obtained by obliquely capturing a mucosal wall in an abnormality candidate region. More specifically, the above-described imaging distance estimation is performed for each pixel position in the abnormality candidate region, and a region where an imaging distance sharply changes (a region where an imaging distance change is locally large) is excluded as the side region. This is because it is difficult to calculate advantageous texture information for specifying an abnormal region in the region where the mucosal surface is obliquely captured. As a result, the side region exclusion unit 205 excludes a side region F3 obtained by obliquely capturing the mucosal wall as illustrated in FIG. 19A. Incidentally, it may be substituted by obtaining a region where a pixel value abruptly changes (a region where a pixel value change locally is large) without performing the estimation of the imaging distance.

Figure 19B:
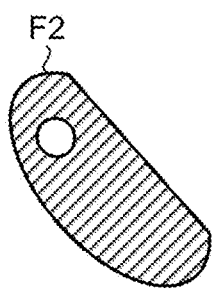
FIG. 19B is a view schematically illustrating a texture information calculation region according to the second modification of the first embodiment.

Subsequently, the specular reflection region exclusion unit 206 excludes a specular reflection region F4 in the abnormality candidate region (Step S304). Regarding the specifying of the specular reflection region F4, for example, a method disclosed in Japanese Patent No. 5658931 is used. The reason why the specular reflection region F4 is excluded is that it is difficult to calculate advantageous texture information for specifying an abnormal region in the specular reflection region F4. As illustrated in FIG. 19B, the information calculation region setting unit 20 sets a region excluding the side region and the specular reflection region from a region within a geometric shape, which has been applied in Step S302, in Steps S301 to S304 is set as a final texture information calculation region. After Step S304, the image processing apparatus 1 returns to the main routine of FIG. 2.

Incidentally, the texture information calculation region may be set by arbitrarily combining the application of the geometric shapes described in the first embodiment and the first and second modifications and the extraction of the active contour, the exclusion of the side region, and the exclusion of the specular reflection region.

According to the second modification of the first embodiment described above, it is possible to set a region that is highly likely to contain the advantageous texture information for specifying the abnormal region in the abnormality candidate region and to sufficiently secure the performance of detecting an abnormal part.

Third Modification

A third modification of the first embodiment will be described. The third modification according to the first embodiment has a different configuration and a different process to be executed of a texture information calculation unit. Hereinafter, the process executed by the texture information calculation unit according to the third modification of the first embodiment will be described after describing the configuration of the texture information calculation unit according to the third modification of the first embodiment. Incidentally, the same configurations as those of the image processing apparatus 1 according to the first embodiment will be denoted by the same reference signs, and the description thereof will be omitted.

Figure 20:
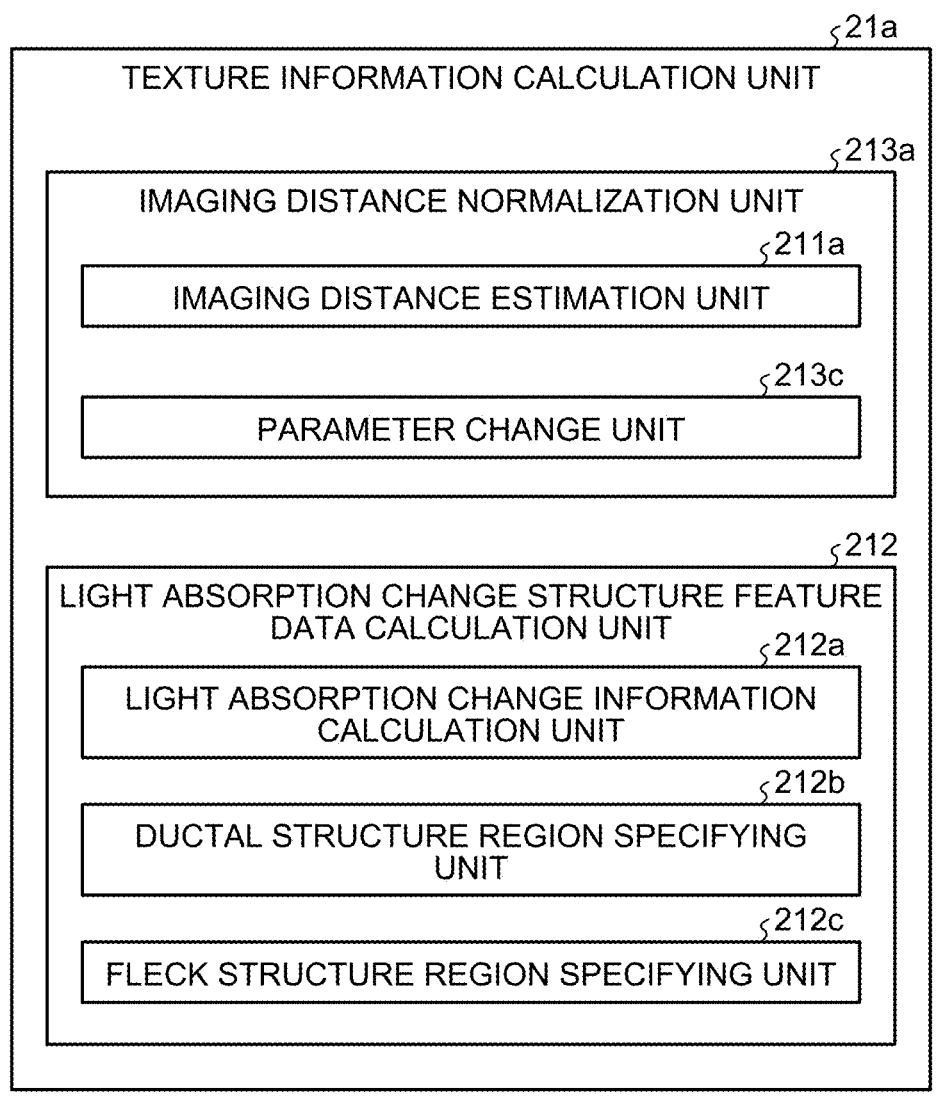
FIG. 20 is a block diagram illustrating a configuration of a texture information calculation unit according to a third modification of the first embodiment.

FIG. 20 is a block diagram illustrating a configuration of the texture information calculation unit according to the third modification of the first embodiment. A texture information calculation unit 21a illustrated in FIG. 20 includes an imaging distance normalization unit 213a in place of the imaging distance normalization unit 211 of the texture information calculation unit 21 according to the first embodiment described above.

The imaging distance normalization unit 213a performs normalization in accordance with an imaging distance to a texture information calculation region. The imaging distance normalization unit 213a includes a parameter change unit 213c in place of the region size change unit 211b of the imaging distance normalization unit 211 according to the first embodiment described above.

The parameter change unit 213c changes a parameter for calculation of texture information based on the imaging distance estimated by the imaging distance estimation unit 211a.

Figure 24:
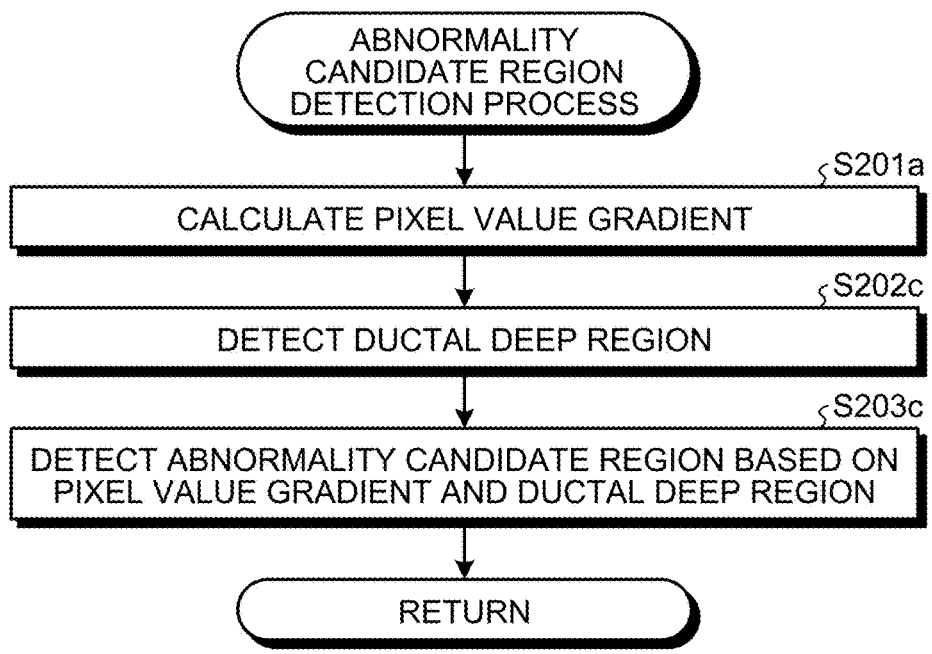
FIG. 24 is a flowchart illustrating an outline of an abnormality candidate region detection process executed by an abnormality candidate region detection unit according to a sixth modification of the first embodiment.

Next, a texture information calculation process executed by the texture information calculation unit 21a will be described. FIG. 24 is a flowchart illustrating an outline of the texture information calculation process executed by the texture information calculation unit 21a. Incidentally, the texture information calculation unit 21a in FIG. 24 executes Step S402a in place of Step S402 of FIG. 7 in the first embodiment described above. The other processes are the same as those of FIG. 7 described above, and thus, the description of the respective processes will be omitted hereinafter. In addition, processes of the third modification of the first embodiment are the same as the processes (see FIG. 2) executed by the image processing apparatus 1 according to the first embodiment described above except for the texture information calculation process executed by the texture information calculation unit 21a, and thus, the description thereof will be omitted.

Figure 21:
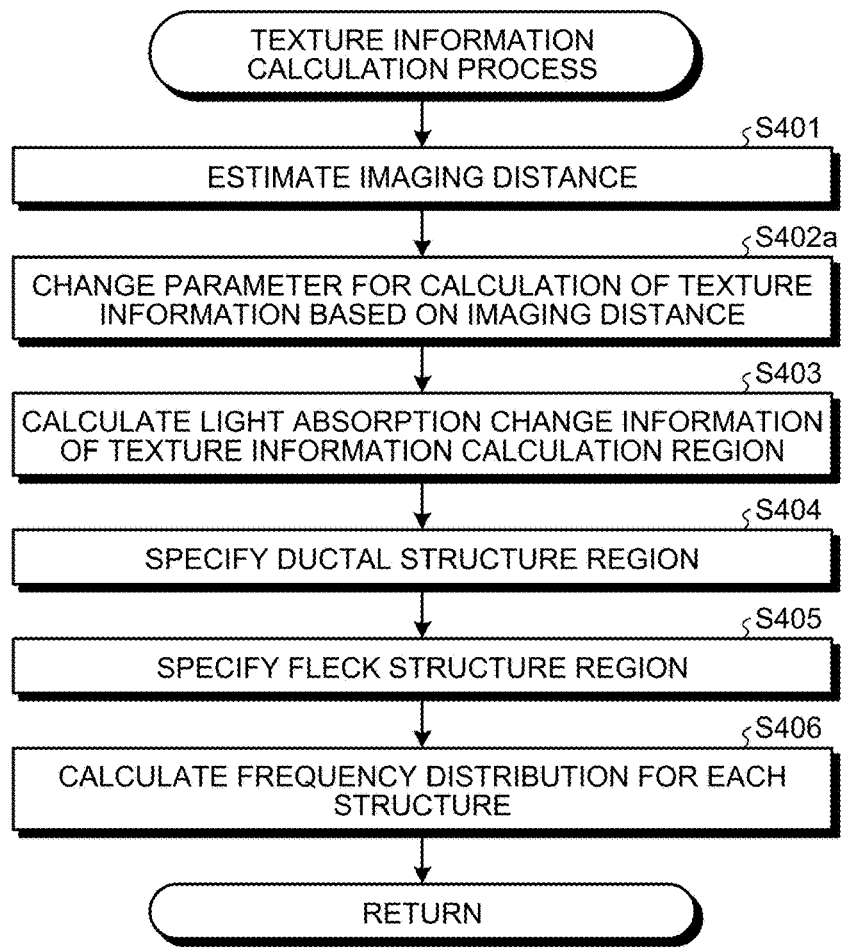
FIG. 21 is a flowchart illustrating an outline of a texture information calculation process executed by a texture information calculation unit according to the third modification of the first embodiment.

As illustrated in FIG. 21, in Step S402a, the parameter change unit 213c changes a parameter for calculation of texture information set by the information calculation region setting unit 20 based on an imaging distance estimated by the imaging distance estimation unit 211a (Step S402a). More specifically, a reference range of a pixel value for calculating parameters to be used to specify a ductal structure region and to specify a fleck structure at the subsequent stages, for example, the shape index and curvedness, based on the imaging distance estimated by the imaging distance estimation unit 211a. This is for performing stable information calculation with respect to an object whose size changes within an image depending on closeness of the imaging distance. For example, the reference range is set to be small in a texture information calculation region that appears small since an imaging distance is distant, and the reference range is set to be large in a texture information calculation region that appears large since an imaging distance is close. As a result, a difference in information calculation depending on the closeness of the imaging distance is hardly caused when the equivalent object appears.

According to the third modification of the first embodiment described above, it is possible to perform stable information calculation even for the object whose size changes within the image depending on the closeness of the imaging distance, and to sufficiently secure the performance of detecting an abnormal part.

Fourth Modification

A fourth modification of the first embodiment will be described. The fourth modification of the first embodiment has a different abnormality candidate region detection process executed by the abnormality candidate region detection unit 10. Hereinafter, the abnormality candidate region detection process executed by the abnormality candidate region detection unit 10 according to the fourth modification of the first embodiment will be described.

Figure 22:
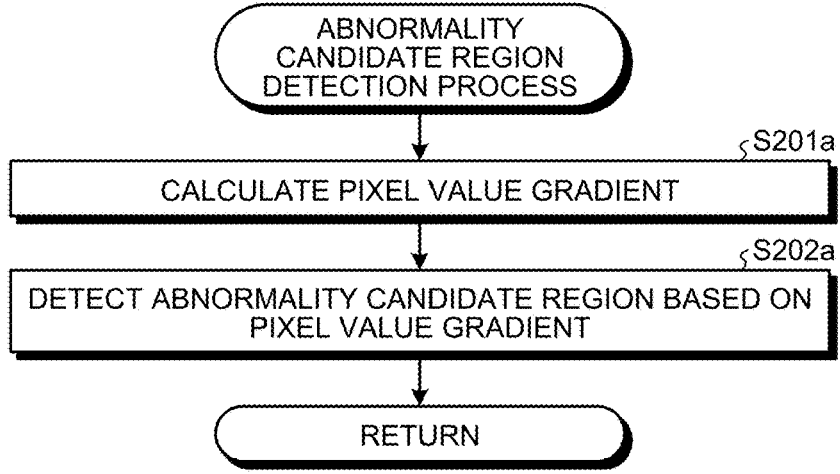
FIG. 22 is a flowchart illustrating an outline of an abnormality candidate region detection process executed by an abnormality candidate region detection unit according to a fourth modification of the first embodiment.

FIG. 22 is a flowchart illustrating an outline of the abnormality candidate region detection process executed by the abnormality candidate region detection unit 10 according to the fourth modification of the first embodiment.

As illustrated in FIG. 22, the abnormality candidate region detection unit 10 calculates a pixel value gradient of an intraluminal image (Step S201a) and detects an abnormality candidate region based on the calculated pixel value gradient (Step S202a). For the detection using the pixel value gradient, a method disclosed in JP 2007-244519 A is used. After Step S202a, the image processing apparatus 1 returns to the main routine of FIG. 2.

According to the fourth modification of the first embodiment described above, it is possible to sufficiently secure the performance of detecting an abnormal portion.

Fifth Modification

A fifth modification of the first embodiment will be described. The fifth modification of the first embodiment has a different abnormality candidate region detection process executed by the abnormality candidate region detection unit 10. Hereinafter, the abnormality candidate region detection process executed by the abnormality candidate region detection unit 10 according to the fifth modification of the first embodiment will be described.

Figure 23:
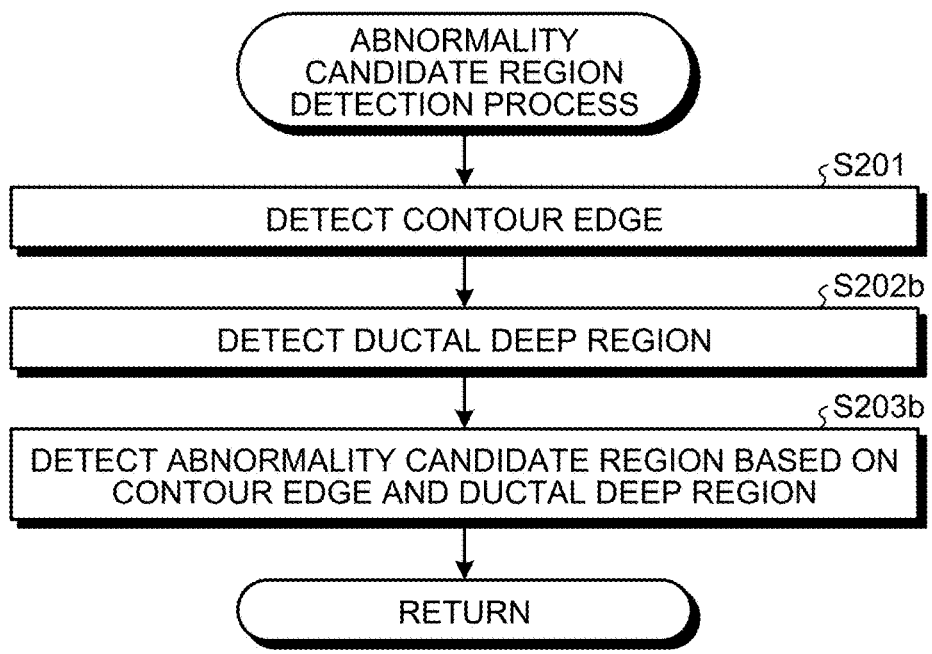
FIG. 23 is a flowchart illustrating an outline of an abnormality candidate region detection process executed by an abnormality candidate region detection unit according to a fifth modification of the first embodiment.

FIG. 23 is a flowchart illustrating an outline of the abnormality candidate region detection process executed by the abnormality candidate region detection unit 10 according to the fifth modification of the first embodiment. In FIG. 23, the abnormality candidate region detection unit 10 executes Steps S202b and S203b in addition to Step S201 of FIG. 3 in the first embodiment described above.

As illustrated in FIG. 23, the abnormality candidate region detection unit 10 detects a ductal deep portion of an intraluminal image in Step S202b. More specifically, a low absorption wavelength component having the lowest degree of absorption and scattering in a body is selected, pixels around a contour edge are excluded from the intraluminal image of the selected low absorption wavelength component, and then, a ductal deep region is detected by detecting a region where a pixel value is equal to or less than a threshold value (see, for example, international application PCT/JP2015/051873, international application PCT/JP2015/062427, or international application PCT/JP2015/062428).

Subsequently, the abnormality candidate region detection unit 10 detects an abnormality candidate region based on the contour edge calculated in Step S201 and the ductal deep region calculated in Step S202b (Step S203b). More specifically, a convex-shaped region on the contour edge and a convex direction thereof are analyzed to detect a convex-shaped region that is convex with respect to a direction of the ductal deep region as an abnormal region. (see, for example, international application PCT/JP2015/051873, international application PCT/JP2015/062427, or international application PCT/JP2015/062428). After Step S203b, the image processing apparatus 1 returns to the main routine of FIG. 2.

According to the fifth modification of the first embodiment described above, it is possible to sufficiently secure the performance of detecting an abnormal portion.

Sixth Modification

A sixth modification of the first embodiment will be described. The sixth modification of the first embodiment has a different abnormality candidate region detection process executed by the abnormality candidate region detection unit 10. Hereinafter, the abnormality candidate region detection process according to the sixth modification of the first embodiment will be described.

FIG. 24 is a flowchart illustrating an outline of the abnormality candidate region detection process executed by the abnormality candidate region detection unit 10 according to the sixth modification of the first embodiment.

As illustrated in FIG. 24, the abnormality candidate region detection unit 10 calculates a pixel value gradient of an intraluminal image (Step S201a) and detects a ductal deep region of an intraluminal image (Step S202c).

Subsequently, the abnormality candidate region detection unit 10 detects an abnormality candidate region based on the pixel value gradient and the ductal deep region calculated in Step S201a (Step S203c). After Step S203c, the image processing apparatus 1 returns to the main routine of FIG. 2.

According to the sixth modification of the first embodiment described above, it is possible to sufficiently secure the performance of detecting an abnormal portion.

Second Embodiment

Next, a second embodiment will be described. The second embodiment has a configuration of a calculation unit different from that of the above-described first embodiment. Hereinafter, the configuration of the calculation unit according to the second embodiment will be described. Incidentally, the same configurations as those of the image processing apparatus 1 according to the first embodiment will be denoted by the same reference signs, and the description thereof will be omitted.

Figure 25:
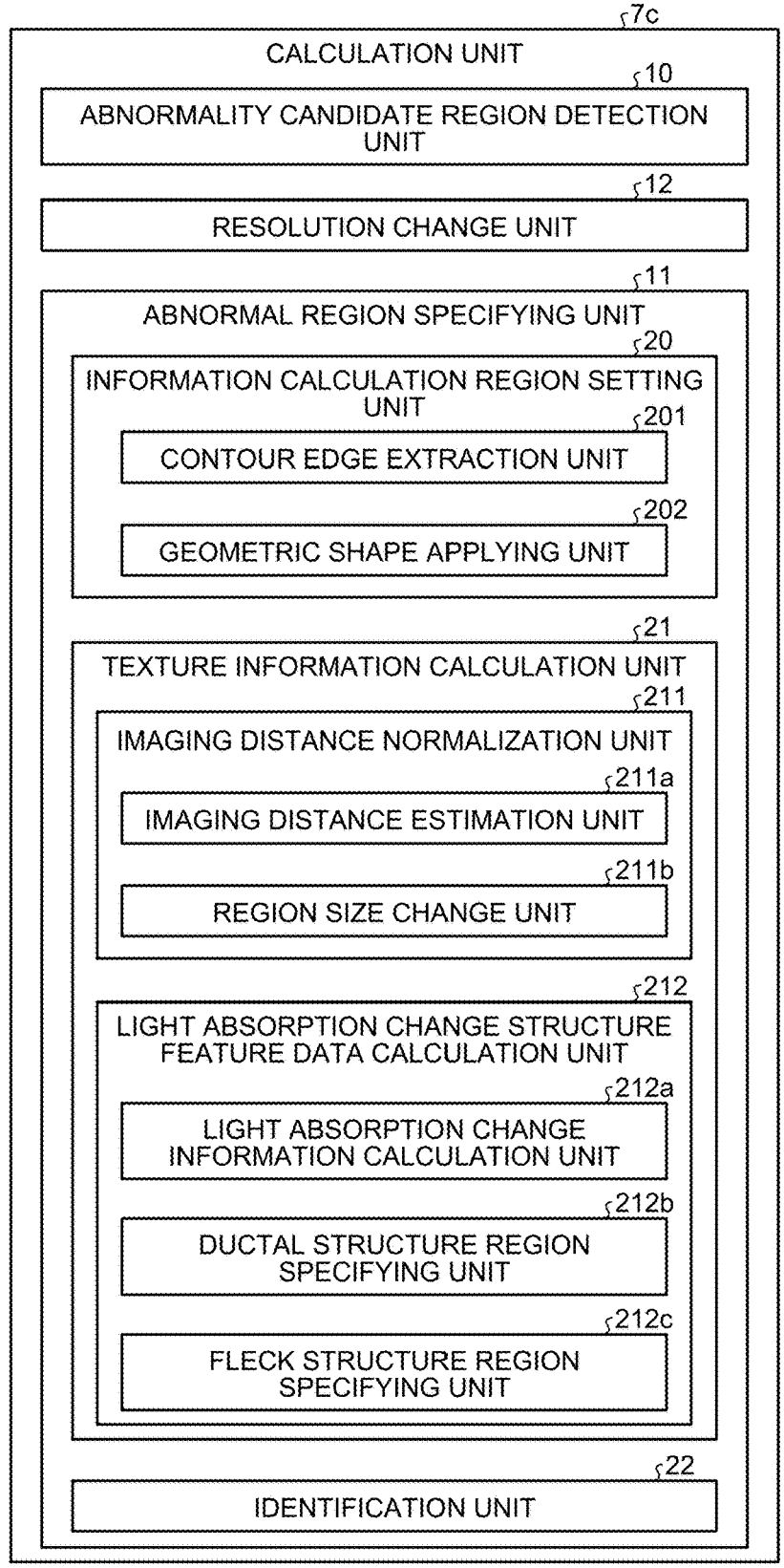
FIG. 25 is a block diagram illustrating a configuration of a calculation unit according to a second embodiment.

FIG. 25 is a block diagram illustrating the configuration of the calculation unit according to the second embodiment. A calculation unit 7c illustrated in FIG. 25 further includes a resolution change unit 12 in addition to the configuration of the calculation unit 7 according to the first embodiment described above.

The resolution change unit 12 changes a resolution of an intraluminal image to be processed in each of the abnormality candidate region detection unit 10 and the abnormal region specifying unit 11. More specifically, the resolution of the intraluminal image to be processed in the abnormal region specifying unit 11 is changed to be higher than the resolution of the intraluminal image to be processed in the abnormality candidate region detection unit 10. That is, the resolution change unit 12 improves the accuracy of specifying the abnormal region by causing the detection of the abnormality candidate region detection unit 10 to be performed using the intraluminal image having the low resolution and the detection of the abnormal region specifying unit 11 to be performed using the intraluminal image having the high resolution. As a result, it is possible to improve the speed of a process of detecting the abnormal region and to sufficiently secure the performance of detecting an abnormal part.

According to the second embodiment described above, it is possible to sufficiently secure the performance of detecting an abnormal portion.

Other Embodiments

In the present disclosure, an image processing program recorded in a recording device can be implemented by being executed on a computer system such as a personal computer and a workstation. In addition, such a computer system may be used in the state of being connected to a device such as another computer system or a server via a public line such as a local area network (LAN), a wide area network (WAN), and the Internet. In this case, the image processing apparatuses according to first and second embodiments and the modifications thereof may be configured to acquire image data of an intraluminal image via these networks, outputs an image processing result to various output devices such as a viewer and a printer connected via these networks, and store the image processing result in a storage device connected via these networks, for example, a recording medium readable by a reading device connected to the network.

Incidentally, the present disclosure is not limited to the first and second embodiments and the modifications thereof, and various inventions can be formed by appropriately combining the plurality of constituent elements disclosed in each of the embodiments and modifications. For example, some constituent elements may be excluded from all the constituent elements illustrated in each of the embodiments and modifications, or constituent elements illustrated in different embodiments and modifications may be appropriately combined.

Incidentally, the sequence of the processes among steps has been illustrated using the terms of "first", "thereafter", "next", and the like in the description of the flowcharts in the present specification. However, the order of processes necessary for implementing the present disclosure is not uniquely determined by those terms. That is, the order of processes in the flowcharts described in the present specification can be changed in a scope without inconsistency.

In addition, the present disclosure is not limited to the above-described embodiments without any change, and the constituent elements can be modified and embodied within a scope not departing from a gist of the disclosure at the implementation stage. In addition, it is possible to form various inventions by appropriately combining a plurality of components disclosed in the above-described embodiments. For example, some constituent elements may be deleted from all the constituent elements described in the above-described embodiments. Further, the constituent elements described in each of the embodiments may be appropriately combined.

In addition, in the specification or the drawings, a term which has been described at least once together with a different term having a broader meaning or the same meaning can be replaced with the different term in any parts of the specification or the drawings. In this manner, various modifications and applications can be made within the scope not departing from the gist of the disclosure.

As above, the present disclosure includes various embodiments that are not described herein, and various types of design alteration or the like can be made within a scope of a technical idea specified by the claims.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   an image processor comprising hardware, the image processor being configured to:
      detects an abnormality candidate region based on a contour edge of a mucosal wall or a surface shape of the mucosal wall in an intraluminal image of a body; and specify an abnormal region based on texture information of the abnormality candidate region,
wherein the specifying of the abnormal region based on texture information of the abnormality candidate region comprises:
setting a calculation region for calculation of the texture information;
calculating the texture information in the calculation region; and
identifying the abnormal region based on the texture information,
the calculating of the texture information in the calculation region comprises:
performing normalization in accordance with an imaging distance to the calculation region; and
calculating feature data based on a light absorption change structure in the calculation region, and
the calculating of the feature data based on the light absorption change structure in the calculation region comprises:
calculating light absorption change information in the calculation region;
specifying a ductal structure region based on the light absorption change information; and
specifying a fleck structure region based on the light absorption change information.

2. The image processing apparatus according to claim 1, wherein the setting of the calculation region for calculation of the text information comprises:
extracting a contour edge of a luminal mucosal wall; and
applying a geometric shape in the contour edge.

3. The image processing apparatus according to claim 1, wherein the setting of the calculation region for calculation of the texture information comprises:
calculating a pixel value gradient intensity in the abnormality candidate region; and
performing active contour extraction based on the pixel value gradient intensity.

4. The image processing apparatus according to claim 1, wherein the setting of the calculation region for calculation of the texture information comprises excluding a side region obtained by obliquely capturing a mucosal wall in the abnormality candidate region.

5. The image processing apparatus according to claim 1, wherein the setting of the calculation region for calculation of the texture information comprises excluding a specular reflection region in the abnormality candidate region.

6. The image processing apparatus according to claim 1, wherein the performing of normalization in accordance with the imaging distance to the calculation region comprises:
estimating an imaging distance; and
changing a region size of the calculation region based on the imaging distance.

7. The image processing apparatus according to claim 1, wherein the performing of normalization in accordance with the imaging distance to the calculation region comprises:
estimating an imaging distance; and
changing a parameter for calculation of the texture information based on the imaging distance.

8. The image processing apparatus according to claim 1, wherein the identifying of the abnormal region based on the texture information comprises determining that the abnormality candidate region is abnormal when a proportion of a fleck structure is large.

9. The image processing apparatus according to claim 1, wherein the detection of the abnormality candidate region based on the contour edge of the mucosal wall or the surface shape of the mucosal wall in the intraluminal image of the body comprises detecting the abnormality candidate region based on pixel value gradient information.

10. The image processing apparatus according to claim 1, wherein the detection of the abnormality candidate region based on the contour edge of the mucosal wall or the surface shape of the mucosal wall in the intraluminal image of the body comprises detecting the abnormality candidate region based on a deep region of a lumen and a contour edge of a mucosal wall.

11. The image processing apparatus according to claim 1, wherein the detection of the abnormality candidate region based on the contour edge of the mucosal wall or the surface shape of the mucosal wall in the intraluminal image of the body comprises detecting the abnormality candidate region based on a deep region of a lumen and pixel value gradient information.

12. The image processing apparatus according to claim 1, wherein the image processor is further configured to change a resolution of an intraluminal image to be processed by the detection of the abnormality candidate region based on the contour edge of the mucosal wall or the surface of the mucosal wall in the intraluminal image and the specification of the abnormal region based on texture information of the abnormality candidate region.

13. The image processing apparatus according to claim 12, wherein the changing of the resolution comprises setting a resolution of an intraluminal image to be processed by the detection of the abnormality candidate region based on the contour edge of the mucosal wall or the surface shape of the mucosal wall in the intraluminal image to be higher than a resolution of an intraluminal image to be processed by the specification of the abnormal region based on texture information of the abnormality candidate region.

14. An image processing method comprising:
detecting an abnormality candidate region based on a contour edge of a mucosal wall or a surface shape of the mucosal wall in an intraluminal image of a body; and
specifying an abnormal region based on texture information of the abnormality candidate region,
wherein the specifying comprising:
setting a calculation region for calculation of the texture information;
calculating the texture information in the calculation region; and
identifying the abnormal region based on the texture information,
the calculating of the texture information in the calculation region comprises:
performing normalization in accordance with an imaging distance to the calculation region; and
calculating feature data based on a light absorption change structure in the calculation region, and
the calculating of feature date based on the light absorption change structure in the calculation region comprising:
calculating light absorption change information in the calculation region;
specifying a ductal structure region based on the light absorption change information; and
specifying a fleck structure region based on the light absorption change information.

15. A non-transitory computer-readable recording medium on which an executable program is recorded, the program instructing a processor of an image processing apparatus to execute:

detecting an abnormality candidate region based on a contour edge of a mucosal wall or a surface shape of the mucosal wall in an intraluminal image of a body;
specifying an abnormal region based on texture information of the abnormality candidate region;
setting a calculation region for calculation of the texture information;
calculating the texture information in the calculation region;
identifying the abnormal region based on the texture information;
performing normalization in accordance with an imaging distance to the calculation region;
calculating feature data based on a light absorption change structure in the calculation region;
calculating light absorption change information in the calculation region;
specifying a ductal structure region based on the light absorption change information; and
specifying a fleck structure region based on the light absorption change information.

* * * * *